(12) United States Patent
Lobanoff

(10) Patent No.: US 12,115,103 B2
(45) Date of Patent: Oct. 15, 2024

(54) SILICONE DEVICE FOR CORNEAL CROSS-LINKING

(71) Applicant: Mark Lobanoff, North Oaks, MN (US)

(72) Inventor: Mark Lobanoff, North Oaks, MN (US)

( * ) Notice: Subject to any disclaimer, the term of this patent is extended or adjusted under 35 U.S.C. 154(b) by 0 days.

(21) Appl. No.: 17/503,559

(22) Filed: Oct. 18, 2021

(65) Prior Publication Data

US 2022/0117783 A1 Apr. 21, 2022

Related U.S. Application Data

(60) Provisional application No. 63/092,759, filed on Oct. 16, 2020.

(51) Int. Cl.
*A61F 9/007* (2006.01)
*A61F 9/00* (2006.01)
*A61F 9/008* (2006.01)

(52) U.S. Cl.
CPC ........ *A61F 9/00736* (2013.01); *A61F 9/0017* (2013.01); *A61F 9/008* (2013.01); *A61F 2009/00893* (2013.01); *A61F 2250/0091* (2013.01)

(58) Field of Classification Search
CPC ............... A61F 9/0017; A61F 9/00736; A61F 9/0079; A61F 9/009; A61F 9/007; A61F 2009/00872; A61F 2009/00893; A61F 2250/0091; A61F 9/00; A61M 1/98; A61M 1/90; A61M 1/95; A61M 2210/0612; A61M 9/008; A61M 9/00806
See application file for complete search history.

(56) References Cited

U.S. PATENT DOCUMENTS

| | | | |
|---|---|---|---|
| 9,724,233 B2 | 8/2017 | Blumenkranz et al. | |
| 2003/0135272 A1* | 7/2003 | Brady | A61F 2/1694 623/6.37 |
| 2006/0287662 A1 | 12/2006 | Berry et al. | |
| 2010/0094249 A1* | 4/2010 | Caswell | A61M 1/92 604/257 |
| 2011/0022035 A1* | 1/2011 | Porter | A61F 9/00825 606/4 |
| 2011/0118654 A1 | 5/2011 | Muller | |
| 2014/0222050 A1* | 8/2014 | Heitel | A61F 9/009 606/166 |

(Continued)

*Primary Examiner* — Leslie A Lopez
*Assistant Examiner* — Jihad Dakkak
(74) *Attorney, Agent, or Firm* — Christensen, Fonder, Dardi & Herbert PLLC; Andrew H. Auderieth

(57) ABSTRACT

A cross-linking device and system are disclosed. In various embodiments, a cross-linking device includes a main body including a sidewall, a corneal gripping portion positioned in the interior cavity and defining an anterior chamber and an ocular chamber and defining an aperture that is configured to allow passage of a portion of a cornea to extend into the anterior chamber. In various embodiments, the device includes a multi-purpose fluid port positioned on the sidewall and defining two or more fluid pathways that connect a pair of exterior ports to an anterior chamber port, and an ocular chamber port respectively to allow for fluids to pass into and out of the interior of the device. In various embodiments the device is constructed from elastomer and, in response to a vacuum, the corneal gripping portion is configured to conform to the eye and seal the anterior chamber.

18 Claims, 9 Drawing Sheets

(56) References Cited

U.S. PATENT DOCUMENTS

| | | |
|---|---|---|
| 2014/0364744 A1 | 12/2014 | Wellhoefer |
| 2015/0088175 A1* | 3/2015 | McWhirter ............ A61F 9/009 606/166 |
| 2016/0106582 A1 | 4/2016 | Campos |
| 2016/0143777 A1 | 5/2016 | Roy et al. |
| 2017/0266044 A1* | 9/2017 | Lake ...................... A61M 11/00 |
| 2018/0271646 A1* | 9/2018 | Marcos Celestino ....................... A61F 9/0079 |
| 2018/0318137 A1* | 11/2018 | Donda .................... A61F 13/02 |
| 2019/0117455 A1 | 4/2019 | Garcia |

* cited by examiner

SILICONE DEVICE FOR CORNEAL CROSS-LINKING

RELATED APPLICATIONS

The present application claims the benefit of U.S. Provisional Patent Application No. 63/092,759, filed Oct. 16, 2020, the disclosure of which is incorporated by reference herein in its entirety.

FIELD OF THE DISCLOSURE

The present disclosure relates to treating conditions of the cornea, and more specifically, to devices and methods for corneal cross-linking.

BACKGROUND

Keratoconus is a disorder of the eye, which can result in thinning and/or weakening of the corneal structure such that the cornea progressively bulges into a conical shape. In many patients, this disorder can result in blurry vision, double vision, nearsightedness, irregular astigmatism, and light sensitivity, among other potential quality-of-life reductions. While the condition may initially be corrected with glasses or soft contact lenses, if the condition continues to progress specialized lenses may be required and, in a small number of people, scarring of the cornea can occur potentially requiring corneal transplantation. In light of these risks, corrective procedures such corneal collagen cross-linking can be used to strengthen the cornea and potentially slow or stop further bulging. Similarly, cross-linking can be performed to preserve the desired reshaping of corneal tissue produced by eye therapies, such as thermokeratoplasty, LASIK surgery, or the like.

Generally, corneal collagen cross-linking involves application of a cross-linking solution to the eye, such as riboflavin or other suitable solution, that is photo-activated by illumination with, for example, an ultraviolet light. The activated solution causes formation of new bonds across collagen strands in the stromal layer of the cornea, which recovers and preserves some of the cornea's mechanical strength. In addition, the oxygen present in the collagen layers of the cornea is known to play a role in the cross-linking reaction. For example, it is generally known that the crosslinking reaction can be limited by the amount of oxygen present. For example, see U.S. Pat. Nos. 8,574,277; 9,644,089; 9,907,698; and 10,010,449, which are incorporated herein by reference in their entirety. In addition, see U.S. Pub. No. 2014/249,509; and 2013/178,821, which are incorporated herein by reference in their entirety. In addition, see Hill et al., *Optimization of Oxygen Dynamics, UV-A Delivery, and Drug Formulation for Accelerated Epi-On Corneal Crosslinking*. Current eye research, 45(4), 450-458, 2020, incorporated herein by reference in its entirety. Further improvements to corneal collagen cross-linking devices and systems would be desirable.

SUMMARY

According to embodiments of the present disclosure, a corneal cross-linking device is disclosed for stabilizing corneal tissue and improving its biomechanical strength. Various embodiments provide benefits in the form of improved devices used to perform cross-linking eye therapies, including an improved ability to implement and increase the concentration of oxygen in cross-linking procedures. The rate of cross-linking in the cornea is related to the concentration of $O_2$ present when the cross-linking agent is irradiated with photo-activating light. As a result, when cross-linking procedures are performed in the presence of high levels of $O_2$, patient outcomes are typically improved with better and more efficient crosslinking of the corneal stromal tissue. This is particularly important when performing an "epi-on" vs. an "epi-off" procedure. Leaving the corneal epithelium on adds extra challenge in getting enough riboflavin to saturate the cornea. In addition, leaving the epithelium on blocks some oxygen access to the stroma during the procedure. However, by having a pressurized high oxygen chamber over the cornea during the application of the UVA light, practitioners will see more effective crosslinking during both epi on and epi off procedures.

Further, various embodiments provide benefits in the form of a device useful for aiding in the treatment of corneal infections. Corneal ulcers and infections can be caused by a variety of organisms such as bacterial, viral, fungal, mold, and amoebic. It can often be hard to treat these corneal infections with eye drops as the medication does not stay in contact with the cornea for very long before it is removed from the eye's surface via blinking and the canalicular drainage mechanism. Because of this, very frequent applications of drops must be given, and the medicated drops must be formulated in very high concentrations in order for the MIC (mean inhibitory concentration) or the MBC (mean bactericidal concentration) to be reached in the corneal stroma. As such, various embodiments provide benefits by allowing for antibiotic/antifungal/antiamoebic drugs to remain in direct contact with the corneal tissue for as long as is desired. In addition, the chamber above the cornea containing the drug can be pressurized, pushing additional drug into the corneal tissue beyond simple diffusion rates based on drug concentration. The chamber allows even distribution across the entire cornea. This should allow drugs to reach much higher concentrations in the corneal stroma than eye drops can achieve. Oxygen gas can also be bubbled through the anti-infective liquid drug in the chamber, creating oxygen free radicals if desired. UVA light can also be delivered through the top of the chamber further killing infectious organisms.

As such, various embodiments of the present disclosure provide a corneal cross-linking device that includes a main body including a sidewall extending from a top portion to a bottom portion and surrounding a central axis, the top portion including a top surface and the bottom portion defining a bottom edge and a primary aperture into an interior cavity defined by the sidewall and the top surface. In one or more embodiments the device includes a corneal gripping portion positioned in the interior cavity and defining a separation between an anterior chamber and an ocular chamber, the ocular chamber shaped via the internal sidewall and the corneal gripping portion to conform to a patient's eye, the corneal gripping portion defining an aperture that is configured to allow passage of a portion of a cornea to extend into the anterior chamber. In one or more embodiments, the device includes a multi-purpose fluid port positioned on the sidewall and defining two or more fluid pathways that connect a pair of exterior ports to an anterior chamber port, and an ocular chamber port respectively to allow fluid to pass into and out of the interior of the device.

In various embodiments the device is constructed from elastomer and the ocular chamber port is attachable to a vacuum source such that suction can be applied between an eye and the interior wall of the ocular chamber such that the corneal gripping portion conforms to the eye and functions to seal off the anterior chamber for insertion of fluid into the anterior chamber without leakage through the aperture between the anterior and ocular chambers.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
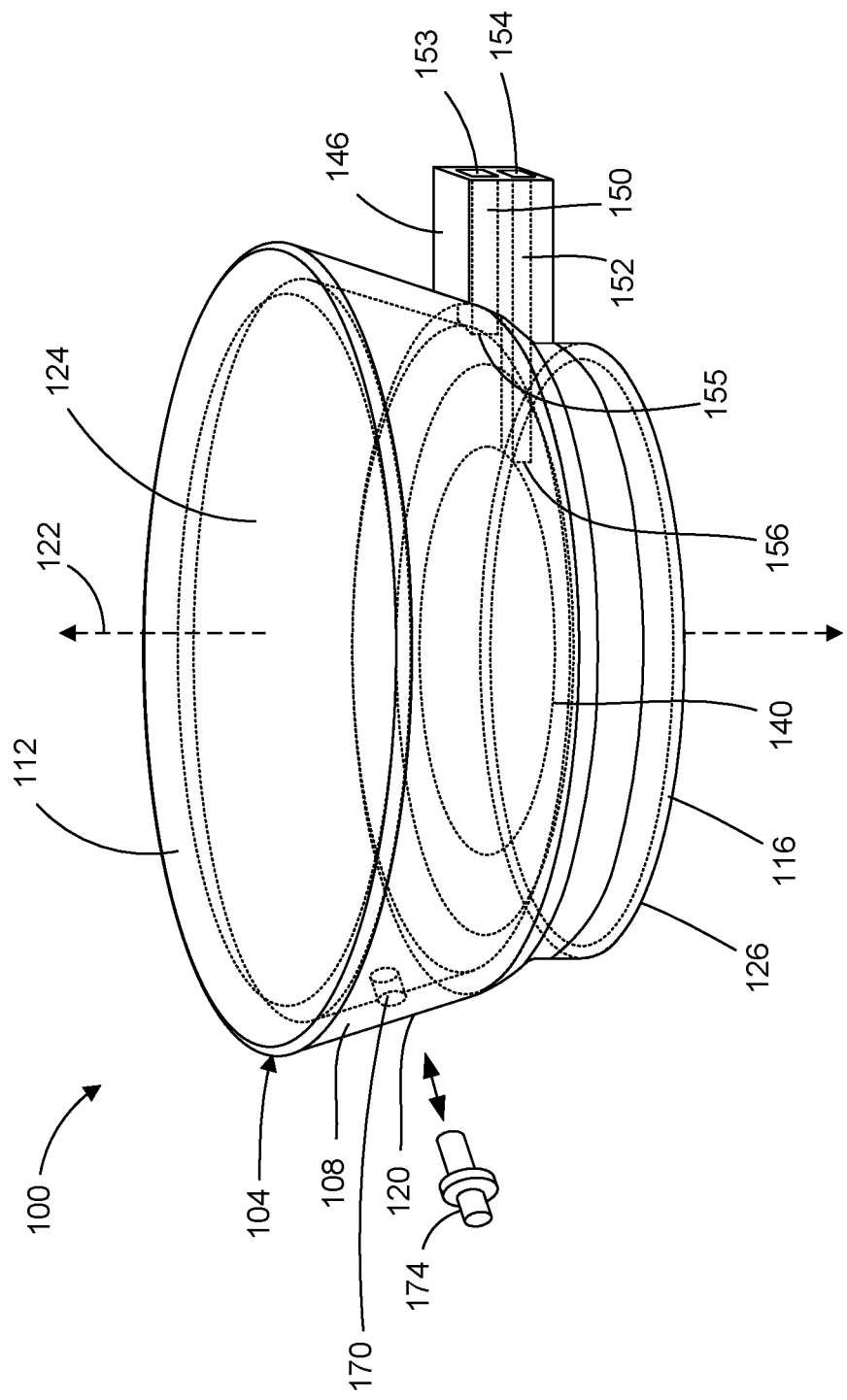
FIG. 1 depicts a perspective view of a cross-linking device, according to one or more embodiments of the disclosure.

While the embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Figure 2:
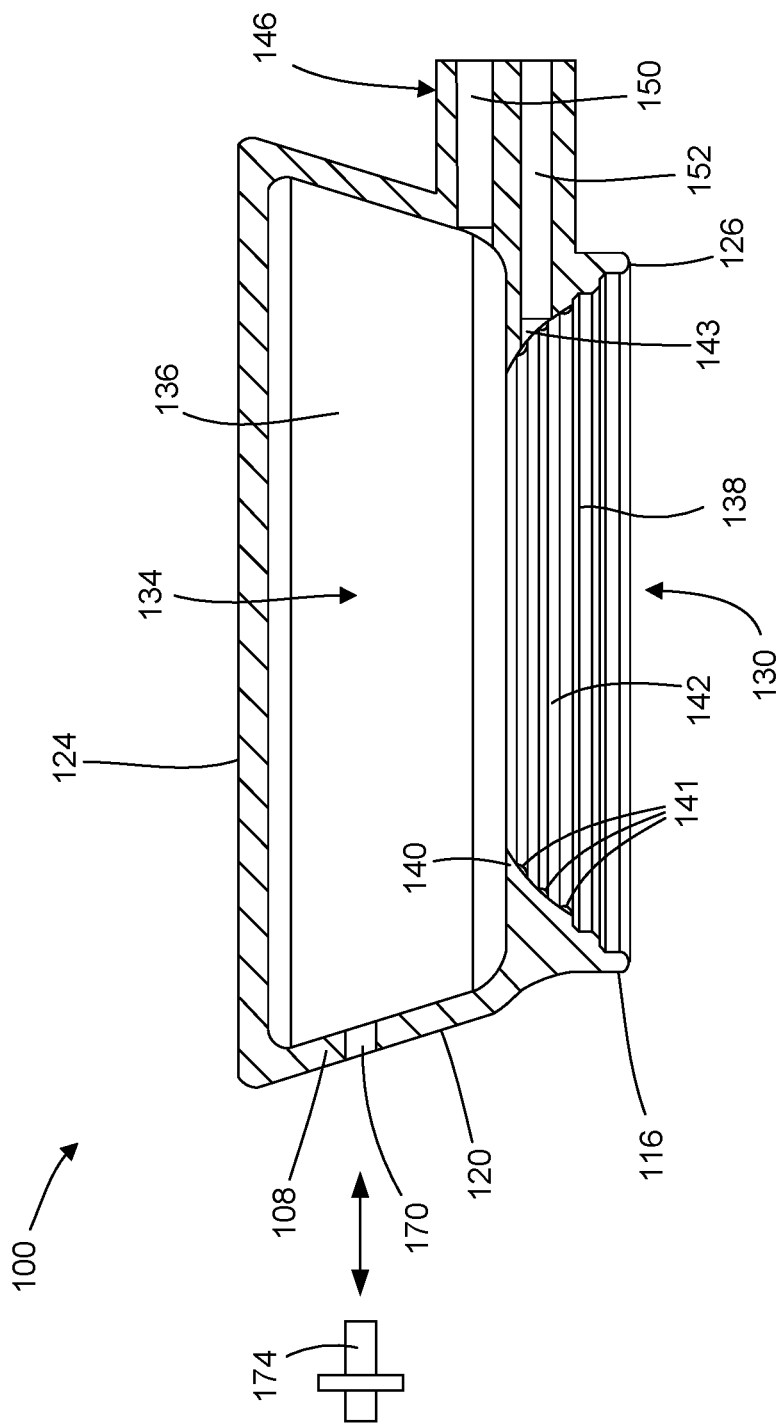
FIG. 2 depicts a cross-sectional plan view of a cross-linking device, according to one or more embodiments of the disclosure.

Referring to FIGS. 1-2 a cross-linking device 100 is depicted according to one or more embodiments. In various embodiments, the device 100 includes a main body 104 that is defined by a sidewall 108 that extends from a top portion 112 of the device to a bottom portion 116. Depicted in FIG. 1, the device 100 has a generally cylindrical or tubular shape with a side portion 120 of the main body 104 extending between the top portion 112 to the bottom portion 116 surrounding a central axis 122.

In one or more embodiments, the top portion 112 defines a top surface 124 while the bottom portion 116 defines a bottom edge 126 and a primary aperture 130 into an interior cavity 134 of the device 100 that is defined by the sidewall 108. In one or more embodiments, the interior cavity 134 includes at least two portions including an anterior chamber 136 and an ocular chamber 138 with a corneal gripping portion 140 positioned between the chambers and defining a boundary therebetween. In one or more embodiments, the corneal gripping portion 140 is a portion of the interior sidewall 142 that is extended inwardly towards the central axis 122 and defines an interior flange and/or ridge with an aperture positioned between the anterior chamber 136 and ocular chamber 138. In various embodiments the corneal gripping portion 140 including one or more circumferential ridges 141 that extend about the interior sidewall 142. In certain embodiments, and described further below, the portion 140 includes a vacuum recess 143 configured to allow for a vacuum to be applied in the ocular chamber for attachment to a cornea while in use. In such embodiments, the circumferential ridges 141 configure the gripping portion 140 to selectively flex at portions of the interior sidewall between the ridges 141 to create a gripping flexing movement that closely conforms the interior sidewall 142 of the device 100 to the cornea while in use.

As such, in one or more embodiments, and described further below the ocular chamber 138 is shaped via the corneal gripping portion 140 to have a curved or generally semi-spherical shape that is configured to conform to and fit to the shape of a patient's eye and/or cornea while in use.

In one or more embodiments, the anterior chamber 136 has a volume that is defined by the placement of the corneal gripping portion 140 along the length of the side portions 120 and/or the diameter of the top surface 124. For example, depicted in FIGS. 1-2 the corneal gripping portion 140 is placed, from the bottom edge 126, approximately one third of the total vertical length of the side portions 120. As a result, approximately two-thirds of the length of the side portions 120 function to define the volume of the anterior chamber while approximately one third of the length of the side portions function to define the volume of the ocular chamber 138. Also depicted, top surface 124 has a diameter that is greater than the diameter of the primary aperture 130 defined by the bottom edge 126. As such, a greater amount of volume is dedicated in the upper portion of the device 100.

In such embodiments, the anterior chamber 136 will have a volume that is larger than the volume of the ocular chamber 138. In some embodiments, the anterior chamber 136 has a volume that is 5% to 50% larger than the volume of the ocular chamber 138. However, in certain embodiments the anterior chamber 136 could have a volume that is 50% larger than the volume of the ocular chamber 138.

In various embodiments, a multi-purpose fluid port 146 is positioned on the side portion 120 of sidewall 108 and defines a pair of fluid pathways 150, 152 that connect a pair of exterior fluid ports 153, 154 to an anterior chamber port 155, and an ocular chamber port 156 respectively. In such embodiments, the fluid pathways 150, 152 define paths to allow for liquid, gasses, and other fluids to pass into and out of the interior of the device. As such, and as used herein the term "fluid" is intended to refer to both liquids and gasses.

In one or more embodiments, the multi-purpose fluid port 146 includes two or more fluid pathways into the interior of the device. In such embodiments, the port 146 allows for multiple fluid inputs or fluid draw functions to occur simultaneously while the device is being used. For example, described further below, the port 146 allows for a vacuum to be applied to one fluid pathway while other fluids could be input or drawn from the device via the other fluid pathway.

Figure 6:
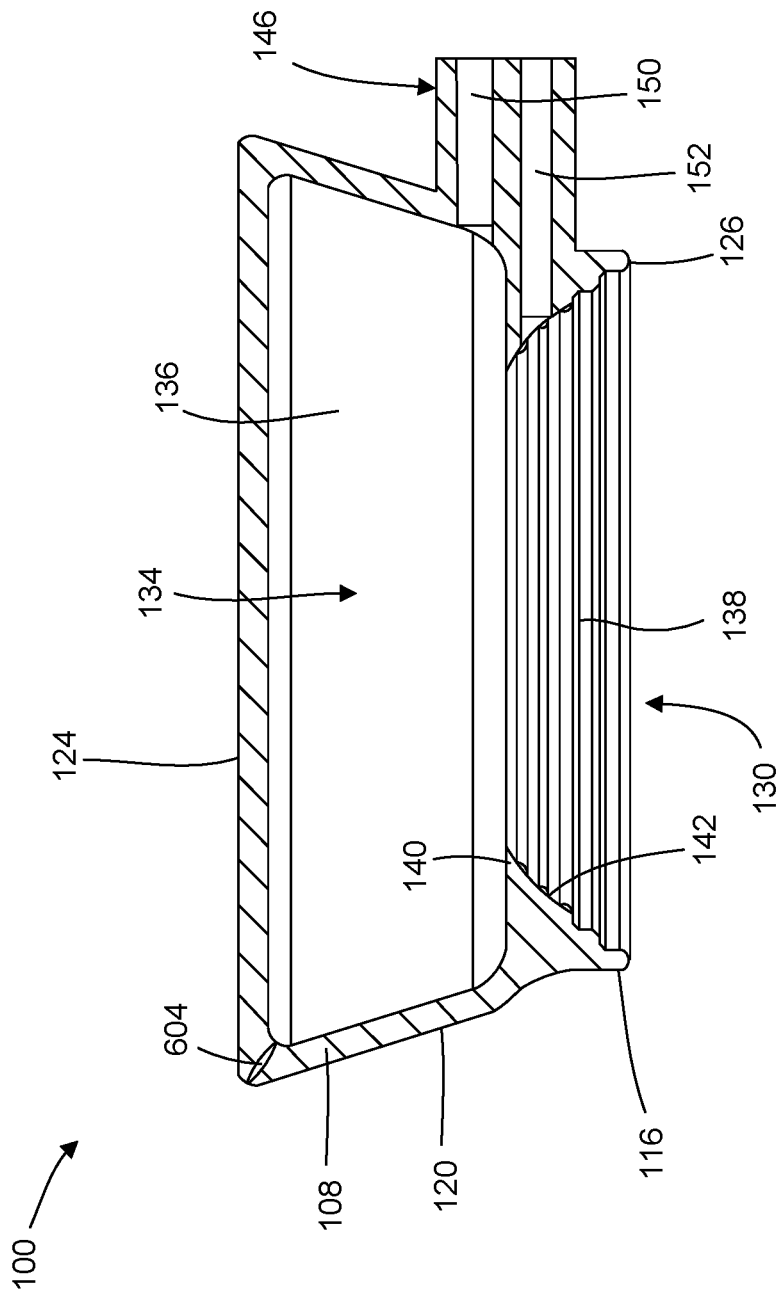
FIG. 6 depicts a cross-sectional plan view of a cross-linking device, according to one or more embodiments of the disclosure.

In one or more embodiments, a pressure release port 170 is additionally included in the side portion 120 of the sidewall. In such embodiments, the port 170 defines an additional fluid pathway into the anterior chamber 136 that can be selectively opened or closed via a plug 174, valve, pressure valve, or other device. In one or more embodiments, the pressure release port 170 allows for pressure equalization of the anterior chamber to prevent damage to the device and/or device pop-off while in use. For example, described further below, when the device is secured to a patient's eye, the port 170 allows for use of a pump to introduce riboflavin or other fluids into the anterior chamber without over-pressurizing the anterior chamber. If over-pressurized the device could rupture or simply pop off the patient's eye while in use. Similarly, the port 170 allows a vacuum to be applied to the chamber to remove riboflavin from the anterior chamber while also preventing collapse of the sidewalls due to pressure of the applied vacuum. Depicted in FIGS. 1-4B, the port 170 is selectively opened and closed via a plastic plug 174 with a circular flange on one end and a handle. However, in various embodiments the port 170 could be selectively opened/closed via a pressure switch, pressure valve, or other device. For example, depicted in FIG. 6, another embodiment of the pressure release port 604 is depicted in the form of a slit valve, which is a self-sealing slit in the top corner of the ring that provides pressure relief and prevents the device from popping off. In such embodiments, no plastic plug or separate device is needed. Instead, the pressure release port 604 is designed to open at specified pressures to allow for equalization into or out of the device.

In one or more embodiments, the device 100 is constructed from one or more of polymer, elastomer, or the like. For example, in various embodiments the device 100 is constructed from one or more of silicone, rubber, latex. In one or more embodiments, the device 100 is constructed as a single piece. However, in some embodiments, the device 100 could be constructed from multiple pieces that are assembled or otherwise fitted together.

In various embodiments, the material of the device 100 is at least partially transparent. For example, in various embodiments the material is sufficiently transparent such that UV light can pass through the material of the device for activation of cross-linking solution within the anterior chamber 136. For example, in various embodiments the top surface 124 the device 100 is constructed from silicone, which has the desired property of allowing excellent transmission of UV light. Further, it additionally allows for clear viewing of a corneal surface by the surgeon while in use.

Figure 3:
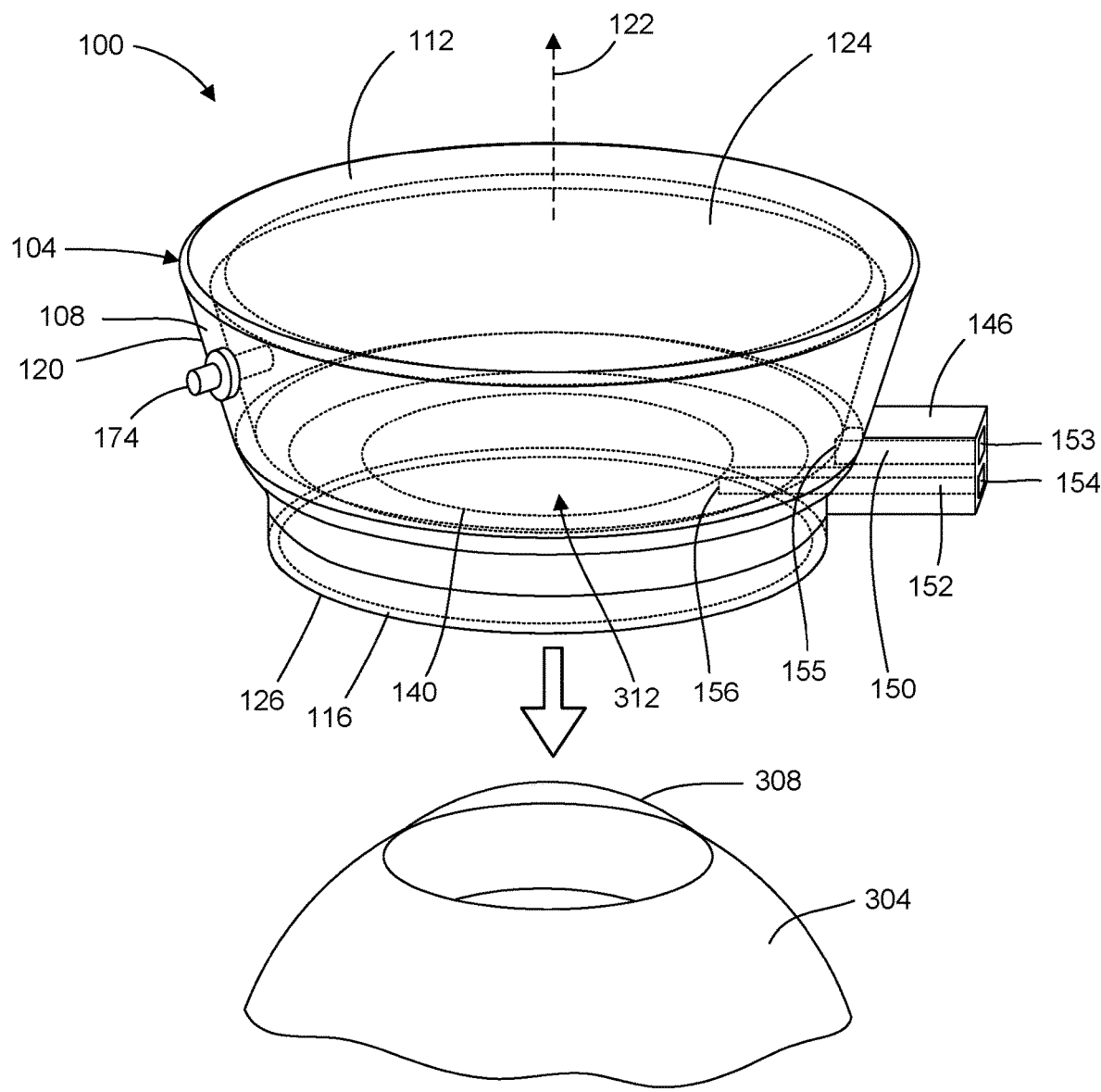
FIG. 3 depicts a perspective view of a cross-linking device in use, according to one or more embodiments of the disclosure.
Figure 4A:
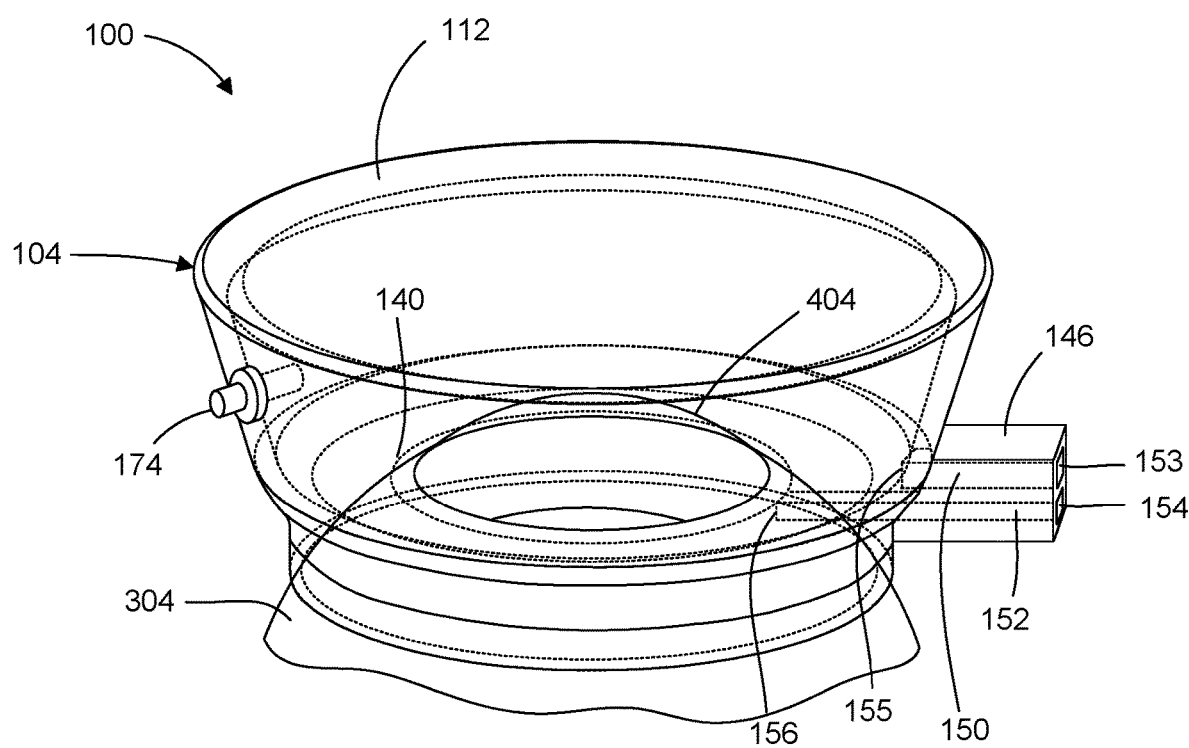
FIGS. 4A-4B depict a perspective view and cross-sectional view of a cross-linking device in use, according to one or more embodiments of the disclosure.
Figure 4B:
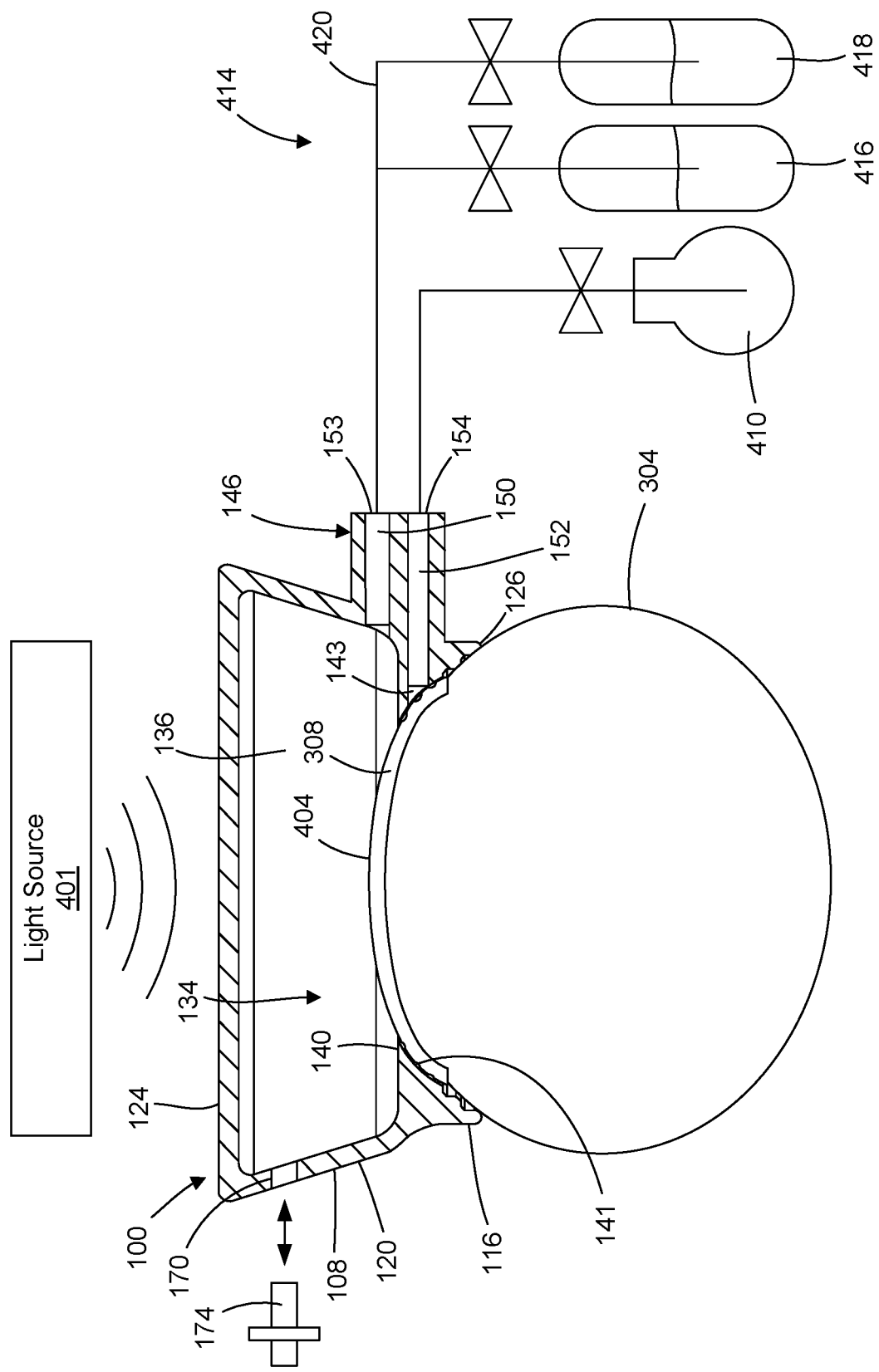

Referring to FIGS. 3 & 4A-4B, perspective views and cross-sectional views of a cross-linking device 100 are depicted while in use, according to one or more embodiments of the disclosure.

In one or more embodiments, the device is centered over and lowered onto a patient's eye 304. As described, the interior sidewall 142 of the ocular chamber 138 has a shape and size configured to conform to the cornea 308. In one or more embodiments, the corneal gripping portion 140 defines a secondary aperture 312 that is configured to allow passage of a portion 404 of the cornea 308 into the anterior chamber 136 such that the portion 404 can be exposed to cross-linking solution and/or UV light source 401 positioned above the device 100.

As described, the ocular chamber port 154 defines a fluid pathway 152 into the ocular chamber 138 of the device 100. As such, when the device 100 is positioned on the eye 304, the ocular chamber port 154 can be attached to a vacuum source 410 and suction can be applied via the fluid pathway 152 to apply suction in the vacuum recess 143 between the eye 304 and the interior wall 142 of the ocular chamber 138 thereby holding the device tightly to the cornea 308.

In various embodiments, because the device 100 is constructed from elastomer or otherwise flexible material, such as silicone, the device 100 will contract and conform against the eye in response to the force of the vacuum when applied between the eye 304 and the interior wall 142. As a result, in various embodiments the corneal gripping portion 140, circumferential ridges 141, and interior sidewalls 142 closely conform to the eye and the corneal gripping portion 140 functions to seal off the anterior chamber 136 and allow for insertion of liquids or other solutions into the anterior chamber 136 without leakage through the aperture 312. As a result, cross-linking solutions can be more closely controlled for exposure onto only the exposed portion 404 of the cornea 308 while keeping the rest of the eye unexposed. In one or more embodiments, the circumferential ridges 141 configure the gripping portion 140 to selectively flex at portions of the interior sidewall between the ridges 141 to create a gripping flexing movement that closely conforms the interior sidewall 142 of the device 100 to the cornea while in use.

In one or more embodiments, the anterior chamber port 153 defines a fluid pathway 150 into the anterior cavity 136. In one or more embodiments, a fluid supply system 414 including a liquid reservoir 416 and oxygen supply 418 are connected to the port 153 by one or more conduits 420 so that, once the anterior chamber 136 has been sealed off using the corneal gripping portion 140 and the vacuum source 410, fluid can be supplied into or out of the anterior chamber using the respective supplies 416, 418. In various embodiments, the liquid supply system 414 may include elements such as pumps, valves, or other elements for controlling the fluid flow. For example, in one or more embodiments, the liquid reservoir 416 includes a cross-linking solution, such as riboflavin, that is first pumped or otherwise inputted through the port 153. After saturation, the liquid can be suctioned out through the port 153 and oxygen next pumped in through the same port 153 via the oxygen supply 418.

Figure 5:
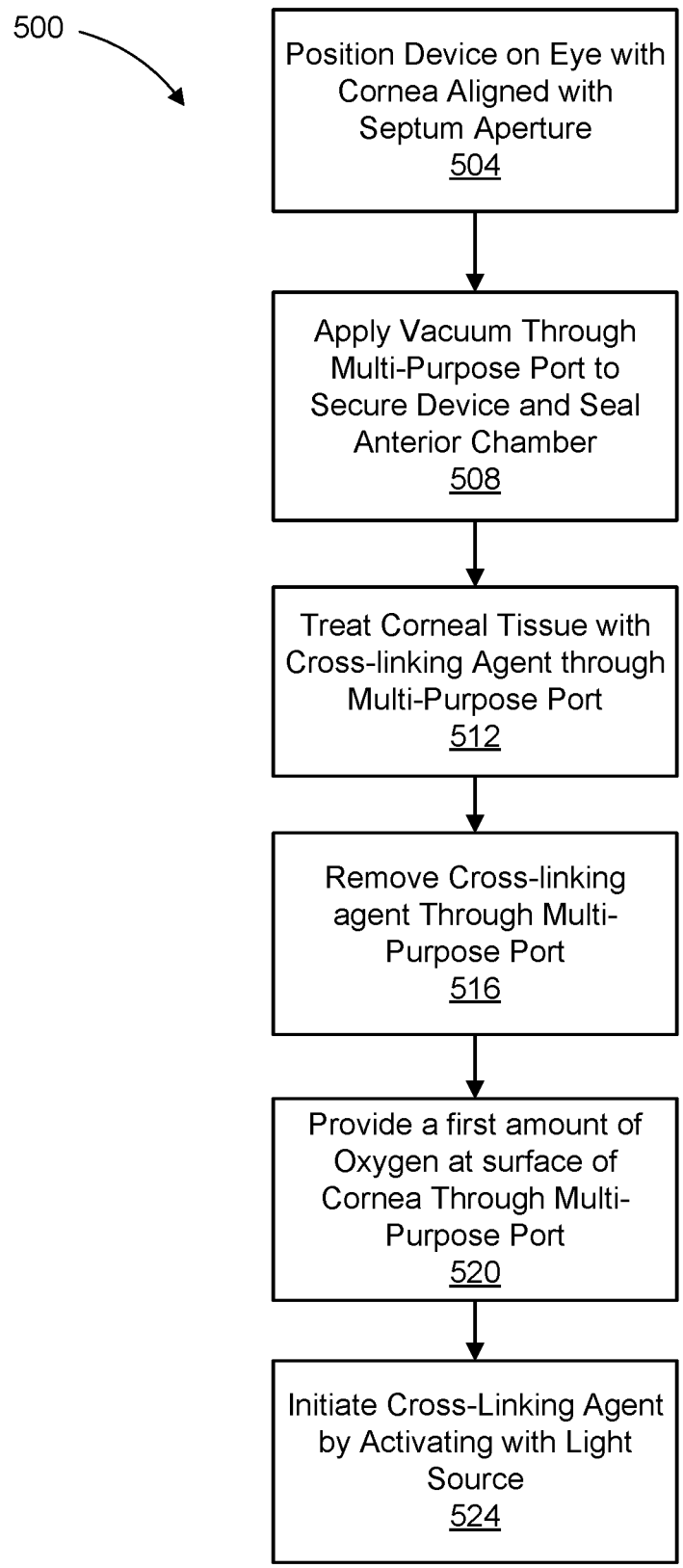
FIG. 5 depicts a method of corneal cross-linking using a cross-linking device, according to one or more embodiments of the disclosure.

Referring to FIG. 5, a method 500 of cross-linking using a cross-linking device is depicted according to one or more embodiments of the disclosure. In one or more embodiments, the method 500 includes, at operation 504, positioning a cross-linking device on an eye. In various embodiments, the cross-linking device is the same or substantially similar as device 100 described and depicted above, including at least two portions including an anterior chamber and an ocular chamber with a corneal gripping portion positioned between the chambers and defining a boundary therebetween. In one or more embodiments, the corneal gripping portion defines a secondary aperture that is configured to allow passage of a portion of the cornea into the anterior chamber. In such embodiments, the cornea of the eye is generally aligned with the aperture such that the portion of the cornea desired for cross-linking will pass through the aperture.

In various embodiments, the method 500 includes, at operation 508, applying a vacuum through a multi-purpose port of the device to secure the device to the eye and seal the anterior chamber. As described, because the device is constructed from elastomer or otherwise flexible material, such as silicone, the device will contract and conform against the eye in response to the force of the vacuum when applied between the eye and the interior wall in the ocular chamber. As a result, in various embodiments the corneal gripping portion and interior sidewalls closely conform to the eye and the corneal gripping portion functions to seal off the anterior chamber and allow for insertion of liquids or other solutions into the anterior chamber without leakage.

In one or more embodiments, the method 500 includes, at operations 512-520, treating the corneal tissue in the anterior chamber with cross-linking agent applied through the multi-purpose port, removing cross-linking agent through the multi-purpose port, and providing a first amount of oxygen at the exposed portion of cornea through the multi-purpose port. As described, the anterior chamber port of the device defines a fluid pathway into the anterior cavity. In one or more embodiments, once the anterior chamber has been sealed off using the corneal gripping portion and the vacuum source, fluid can be supplied into or out of the anterior chamber using respective supplies.

In one or more embodiments, the method 500 includes, at operation 524, initiating cross-linking agent by activating the agent with a light source. In various embodiments, the light source is a UV light that initiates cross-linking activity by causing the applied cross-linking agent, such as riboflavin, to release reactive oxygen radicals in the corneal tissue. The agent acts as a sensitizer to convert $O_2$ into singlet oxygen, which causes cross-linking within the corneal tissue.

While in various embodiments the method 500 involves treating the corneal tissue using cross-linking agent and activating the agent with a light source, it is intended that a method of treatment could include treating the cornea with any suitable medication and/or applying light to the cornea through the device. For example, in various embodiments a method could include treating the cornea with antibiotic/antifungal/antiamoebic drugs and using the device to insert the medication through the multi-purpose port such that the medication will remain in direct contact with the corneal tissue for as long as is desired. In addition, the chamber above the cornea containing the drug can be pressurized, pushing additional drug into the corneal tissue beyond simple diffusion rates based on drug concentration. The chamber allows even distribution across the entire cornea. This should allow drugs to reach much higher concentrations in the corneal stroma than eye drops can achieve. Oxygen gas can also be bubbled through the anti-infective liquid drug in the chamber, creating oxygen free radicals if desired. UVA light can also be delivered through the top of the chamber further killing infectious organisms.

Figure 7:
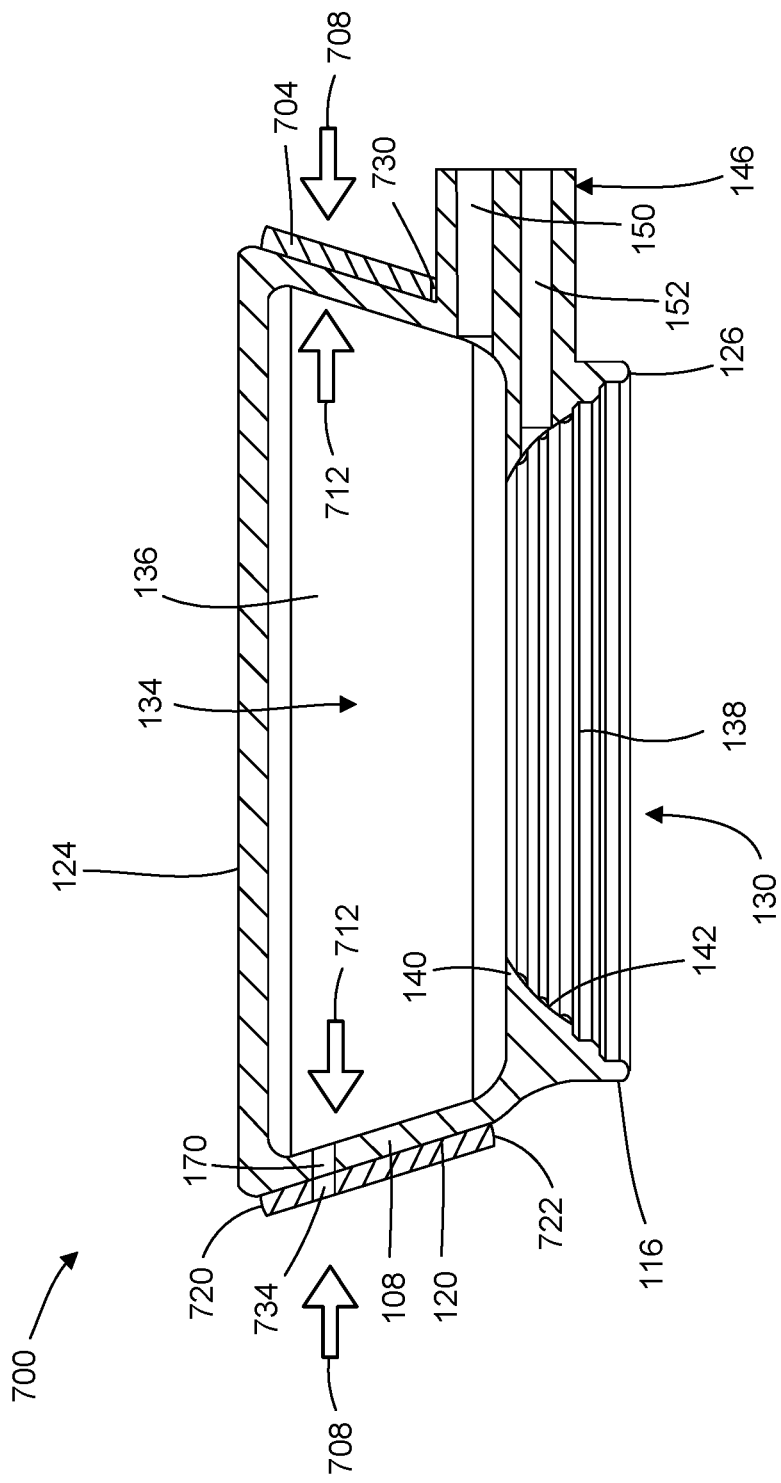
FIG. 7 depicts a cross-sectional plan view of a cross-linking device with an exterior support sidewall, according to one or more embodiments of the disclosure.
Figure 8:
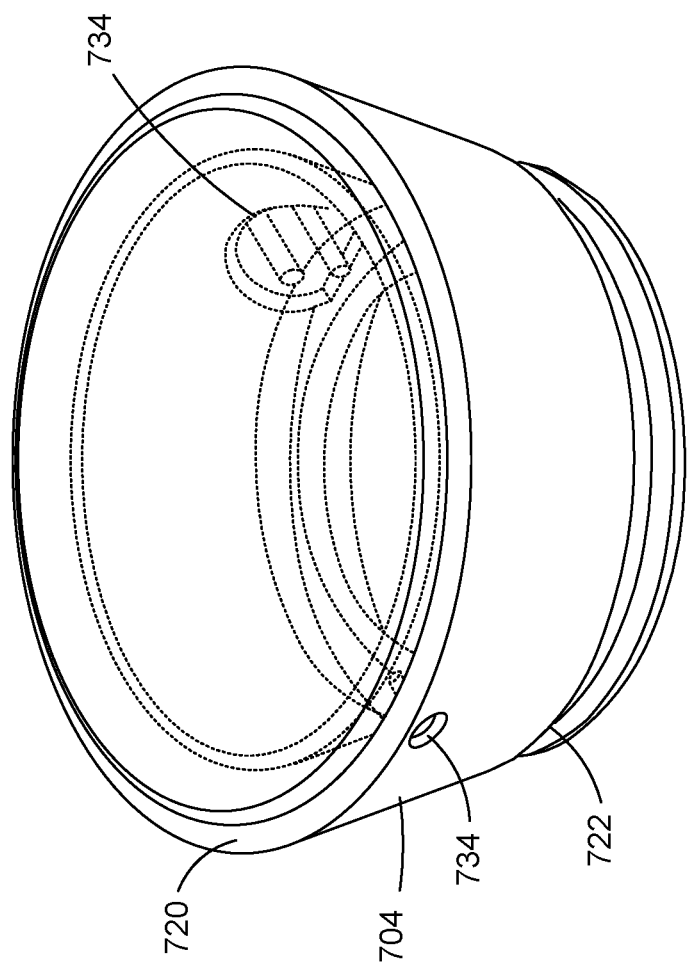
FIG. 8 depicts a perspective view of a cross-linking device with an exterior support sidewall, according to one or more embodiments of the disclosure.

Referring to FIGS. 7-8, a cross-sectional plan view and perspective view of a cross-linking device 700 with an exterior support sidewall 704 is depicted, according to one or more embodiments of the disclosure. As described above, with reference to FIGS. 1-2, the device 700 includes a main body 104 defined by a sidewall 108 that extends from a top portion 112 to a bottom portion 116. For example, the device 100 has a generally cylindrical or tubular shape with a side portion 120 of the main body 104 extending between the top portion 112 to the bottom portion 116 surrounding a central axis. In one or more embodiments, the top portion 112 defines a top surface 124 while the bottom portion 116 defines a bottom edge 126 and a primary aperture 130 into an interior cavity 134 of the device 100 that is defined by the sidewall 108. In one or more embodiments, the interior cavity 134 includes at least two portions including an anterior chamber 136 and an ocular chamber 138 with a corneal gripping portion 140 positioned between the chambers and defining a boundary therebetween. A multi-purpose fluid port 146 is positioned on the side portion 120 of sidewall 108 and defines a pair of fluid pathways 150, 152 that connect a pair of exterior fluid ports 153, 154 to an anterior chamber port 155, and an ocular chamber port 156 respectively. In such embodiments, the fluid pathways 150, 152 define paths to allow for liquid, gasses, and other fluids to pass into and out of the interior of the device. A pressure release port 170 is additionally included in the side portion 120 of the sidewall. In such embodiments, the port 170 defines an additional fluid pathway into the anterior chamber 136 that can be selectively opened or closed via a plug 174, valve, pressure valve, or other device. In one or more embodiments, the pressure release port 170 allows for pressure equalization of the anterior chamber to prevent damage to the device and/or device pop-off while in use.

Depicted in FIGS. 7-8, the device 700 additionally includes a rigid sidewall support 704 that, in various embodiments, is a relatively inflexible ring or shell that, when combined with the relatively flexible sidewall 108, assists in maintaining the shape of the sidewall 108 in response to forces of compression or expansion. For example, in various embodiments the sidewall support 704 is constructed from a plastic, metal, or other material with a lower flexibility as compared to the remainder of the device to assist the sidewall 108 to maintain its shape in a radial direction, relative to the central axis. In various embodiments, the support 704 has an annular shape and extends from a top portion 720 to a bottom portion 722 and can include various apertures 730, 734 that correspond to the multi-purpose fluid port 146 and the pressure release port 170, respectively.

As such, in various embodiments the sidewall support 704, by maintaining the shape of the sidewall 108 can prevent damage to the device and/or device pop-off while in use. For example, when the device is secured to a patient's eye, the sidewall support 704 resists compressing forces, indicated by arrows 708. Such force 708 can occur during use from a patient's eyelid, for example where a patient voluntarily or involuntarily squeezes down on the device 700 by attempting to close their eyelid while the device 700 is attached. Similarly, in various embodiments the sidewall support 704 also resists expansion forces, indicated by arrows 712. Such forces can also result in pop off, for example during the use of a pump to introduce riboflavin or other fluids into the anterior chamber.

Depicted in FIGS. 7-8, while the sidewall support 704 is depicted a single ring or shell that surrounds the exterior of the device 700, in certain embodiments the sidewall support 704 could include multiple rings. In some embodiments, the sidewall support 704 could be positioned in the interior of the device 700. For example, the support could be positioned in the interior of the anterior chamber. In some embodiments the support 704 could be positioned in the sidewall 108. For example, the support 704 could be molded or otherwise inserted within the sidewall 108. In certain embodiments, the sidewall support could comprise one or more wires or strands that are looped around the sidewall 108 or included in the sidewall 108 as structural support.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A cross-linking device, comprising:
a main body including an uninterrupted sidewall extending from a top surface to a bottom edge and surrounding a central axis, the top surface having a radius from the central axis to the sidewall, a top portion including the top surface and a bottom portion including the bottom edge and defining a primary aperture into an interior cavity defined by the sidewall and the top surface;
a corneal gripping portion positioned in the interior cavity and defining an anterior chamber and an ocular chamber, the ocular chamber shaped via the corneal gripping portion to conform to an eye, the corneal gripping portion defining a secondary aperture that is configured to allow passage of a portion of a cornea to extend into the anterior chamber, and the corneal gripping portion including one or more interior circumferential ridges where the circumferential ridges configure the gripping portion to selectively flex at portions of an interior sidewall adjacent to the one or more ridges to create a flexing movement that conforms the corneal gripping portion to a cornea when suction is applied between an inserted eye and an interior wall of the ocular chamber;
a fluid port positioned on the sidewall and defining two or more fluid pathways that connect a pair of exterior ports to an anterior chamber port, and an ocular chamber port respectively to allow fluid to pass into and out of the interior cavity of the device; and
an anterior chamber pressure port in the sidewall of the main body for selectively opening and closing for equalization of pressure in the anterior chamber;
wherein the device is constructed exclusively from elastomer and wherein the ocular chamber port is attachable to a vacuum source such that suction can be applied between an eye and the interior wall of the ocular chamber and wherein, in response, the corneal gripping portion conforms to an inserted eye and functions to seal off the anterior chamber for insertion of liquids or other solutions into the anterior chamber.

2. The cross-linking device of claim 1, wherein the device is constructed from an elastomer including one or more of silicone, latex, and rubber.

3. The cross-linking device of claim 1, wherein the top surface is constructed from silicone.

4. The cross-linking device of claim 1, wherein, when suction is applied between an inserted eye and the interior wall of the ocular chamber, fluids are input or drawn from the device via the fluid port.

5. The cross-linking device of claim 1, further comprising:
a sidewall support comprising an exterior shell surrounding a portion of the main body, the sidewall support constructed from a material having a relatively lower flexibility than the main body portion for maintaining the shape of the main body portion in a radial direction relative to the central axis.

6. The cross-linking device of claim 1, wherein the device is at least partially transparent.

7. The cross-linking device of claim 1, wherein the anterior chamber has a volume that is larger than the volume of the ocular chamber.

8. The cross-linking device of claim 1, wherein the anterior chamber has a volume that is defined by the placement of the corneal gripping portion along the length of the sidewall and the diameter of the top surface.

9. The cross-linking device of claim 8, wherein the anterior chamber has a volume that is 5% to 50% larger than a volume of the ocular chamber.

10. The cross-linking device of claim 8, wherein approximately two-thirds of the length of the sidewall defines the volume of the anterior chamber while approximately one-third of the length of the sidewall defines the volume of the ocular chamber.

11. The cross-linking device of claim 1, wherein the anterior chamber pressure port is a slit valve.

12. A cross-linking system, comprising:
a single-piece elastomeric cross-linking device including:
a main body including a sidewall extending from a top portion to a bottom portion and surrounding a central axis, the top portion including a top surface having a radius from the central axis to the sidewall and the bottom portion defining a bottom edge and a primary aperture into an interior cavity of an enclosure defined by the sidewall and the top surface;
a corneal gripping portion positioned in the interior cavity and defining an anterior chamber and an ocular chamber, the ocular chamber shaped via the corneal gripping portion to conform to an eye, the corneal gripping portion defining a secondary aperture that is configured to allow passage of a portion of a cornea to extend into the anterior chamber, and the corneal gripping portion including one or more interior circumferential ridges where the circumferential ridges configure the gripping portion to selectively flex at portions of an interior sidewall adjacent to the one or more ridges to create a flexing movement that conforms the corneal gripping portion to a cornea when suction is applied between an inserted eye and interior wall of the ocular chamber;
a fluid port positioned on the sidewall and defining two or more fluid pathways that connect a pair of exterior ports to an anterior chamber port, and an ocular chamber port respectively to allow fluid to pass into and out of the interior cavity of the device; and
an anterior chamber pressure port in the sidewall of the main body for selectively opening and closing for equalization of pressure in the anterior chamber;
wherein the ocular chamber port is attachable to a vacuum source such that suction can be applied between an eye and the interior wall of the ocular chamber and wherein, in response, the corneal gripping portion conforms to an inserted eye and functions to seal off the anterior chamber for insertion of liquids or other solutions into the anterior chamber;
a vacuum source connected to the ocular chamber via the fluid port; and
a fluid supply system including a liquid reservoir and an oxygen supply connected to the anterior chamber via the fluid port;
wherein once the anterior chamber has been sealed off using the corneal gripping portion and the vacuum source, fluid is moved into or out of the anterior chamber using the fluid supply system.

13. The cross-linking system of claim 12, wherein the anterior chamber has a volume that is larger than the volume of the ocular chamber.

14. The cross-linking system of claim 12, wherein the top surface is constructed from silicone.

15. The cross-linking system of claim 12, wherein the anterior chamber has a volume that is defined by the placement of the corneal gripping portion along the length of the sidewall and the diameter of the top surface.

16. The cross-linking system of claim 15, wherein the anterior chamber has a volume that is 5% to 50% larger than a volume of the ocular chamber.

17. The cross-linking system of claim 15, wherein approximately two-thirds of the length of the sidewall defines the volume of the anterior chamber while approximately one-third of the length of the sidewall defines the volume of the ocular chamber.

18. The cross-linking system of claim 12, further comprising:
 a sidewall support comprising an exterior shell surrounding a portion of the main body, the sidewall support constructed from a material having a relatively lower flexibility than the main body portion for maintaining the shape of the main body portion in a radial direction relative to the central axis.

\* \* \* \* \*